(12) United States Patent
Beck

(10) Patent No.: US 8,908,937 B2
(45) Date of Patent: Dec. 9, 2014

(54) METHOD AND DEVICE FOR DIGITAL IMAGE TEMPLATING

(75) Inventor: Paul Richard Beck, Chicago, IL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 287 days.

(21) Appl. No.: 12/832,724

(22) Filed: Jul. 8, 2010

(65) Prior Publication Data

US 2012/0008848 A1    Jan. 12, 2012

(51) Int. Cl.
*G06K 9/00* (2006.01)
*G06T 7/60* (2006.01)
*A61B 19/00* (2006.01)

(52) U.S. Cl.
CPC . *G06T 7/60* (2013.01); *A61B 19/50* (2013.01); *A61B 2019/502* (2013.01); *A61B 2019/508* (2013.01); *G06T 2207/10116* (2013.01); *G06T 2207/20092* (2013.01); *G06T 2207/30008* (2013.01); *G06T 2207/30052* (2013.01)
USPC ........................................ 382/128

(58) Field of Classification Search
None
See application file for complete search history.

(56) References Cited

U.S. PATENT DOCUMENTS

| | | | |
|---|---|---|---|
| 5,360,446 A | 11/1994 | Kennedy | |
| 5,400,513 A | 3/1995 | Duffield | |
| 5,682,886 A | 11/1997 | Delp et al. | |
| 5,769,092 A | 6/1998 | Williamson, Jr. | |
| 5,799,055 A * | 8/1998 | Peshkin et al. | 378/42 |
| 5,832,422 A | 11/1998 | Wiedenhoefer | |
| 6,205,411 B1 | 3/2001 | DiGioia et al. | |
| 6,272,247 B1 | 8/2001 | Manickam et al. | |
| 6,334,157 B1 | 12/2001 | Oppermann et al. | |
| 6,342,905 B1 | 1/2002 | Diedrich et al. | |
| 6,424,332 B1 | 7/2002 | Powell | |
| 6,459,948 B1 | 10/2002 | Ateshian et al. | |
| 6,573,915 B1 * | 6/2003 | Sivan et al. | 715/781 |
| 6,701,174 B1 | 3/2004 | Krause et al. | |
| 6,772,026 B2 | 8/2004 | Bradbury et al. | |
| 6,932,842 B1 | 8/2005 | Litschko et al. | |
| 7,158,692 B2 * | 1/2007 | Chalana et al. | 382/294 |
| 7,383,073 B1 | 6/2008 | Abovitz et al. | |

(Continued)

FOREIGN PATENT DOCUMENTS

EP    2405336 A1    11/2012

OTHER PUBLICATIONS

Wikipedia, "Distributed Computing", Jan. 5, 2009.*

(Continued)

*Primary Examiner* — Stephen R Koziol
*Assistant Examiner* — Raphael Schwartz
(74) *Attorney, Agent, or Firm* — Harness, Dickey

(57) ABSTRACT

Methods and devices for orthopedic templating are presented. In an example embodiment, a template object is displayed on an output device that is also displaying a target object and a reference object. The target object may be displayed at an unknown magnification level, while the reference object is of a known size. By measuring the size of the reference object as displayed, the magnification level of the target object can be determined. Then, the template object or the target object can be sized such that the template object substantially matches at least a section of the target object. Once matched, the template object may be overlaid, transparently or semi-transparently, on or with the target object. The template object may also be rotated or moved so that it aligns with at least the matched part of the target object.

25 Claims, 8 Drawing Sheets

(56) References Cited

U.S. PATENT DOCUMENTS

| | | |
|---|---|---|
| 7,388,972 B2 | 6/2008 | Kitson |
| 7,468,075 B2 | 12/2008 | Lang et al. |
| 7,534,263 B2 | 5/2009 | Burdulis, Jr. et al. |
| 7,981,158 B2 | 7/2011 | Fitz et al. |
| 7,983,777 B2 | 7/2011 | Melton et al. |
| 8,066,708 B2 | 11/2011 | Lang et al. |
| 8,077,950 B2 | 12/2011 | Tsougarakis et al. |
| 2004/0151399 A1 | 8/2004 | Skurdal et al. |
| 2005/0038338 A1 | 2/2005 | Bono et al. |
| 2005/0059873 A1 | 3/2005 | Glozman et al. |
| 2005/0162419 A1 | 7/2005 | Kim et al. |
| 2006/0242159 A1 | 10/2006 | Bishop et al. |
| 2006/0287733 A1 | 12/2006 | Bonutti |
| 2007/0118055 A1 | 5/2007 | McCombs |
| 2007/0118243 A1 | 5/2007 | Schroeder et al. |
| 2007/0198022 A1 | 8/2007 | Lang et al. |
| 2007/0226986 A1 | 10/2007 | Park et al. |
| 2007/0272747 A1 | 11/2007 | Woods et al. |
| 2008/0063302 A1 | 3/2008 | Russak et al. |
| 2008/0063304 A1 | 3/2008 | Russak et al. |
| 2008/0148167 A1 | 6/2008 | Russak et al. |
| 2008/0180406 A1 | 7/2008 | Han et al. |
| 2008/0189358 A1 | 8/2008 | Charles |
| 2008/0319448 A1 | 12/2008 | Lavallee et al. |
| 2009/0043556 A1 | 2/2009 | Axelson et al. |
| 2009/0089081 A1 | 4/2009 | Haddad |
| 2009/0222014 A1 | 9/2009 | Bojarski et al. |
| 2009/0259967 A1 | 10/2009 | Davidson et al. |
| 2009/0306676 A1 | 12/2009 | Lang et al. |
| 2009/0312805 A1 | 12/2009 | Lang et al. |
| 2010/0030231 A1 | 2/2010 | Revie et al. |
| 2010/0080491 A1 | 4/2010 | Ohnishi |
| 2010/0134425 A1 | 6/2010 | Storrusten |
| 2010/0217270 A1 | 8/2010 | Polinski et al. |
| 2010/0274534 A1 | 10/2010 | Steines et al. |
| 2010/0281678 A1 | 11/2010 | Burdulis, Jr. et al. |
| 2010/0295803 A1 | 11/2010 | Kim et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305907 A1 | 12/2010 | Fitz et al. |
| 2010/0329530 A1 | 12/2010 | Lang et al. |
| 2011/0029091 A1 | 2/2011 | Bojarski et al. |
| 2012/0194505 A1 | 8/2012 | Beck |

OTHER PUBLICATIONS

Brannigan et al., A Framework for "Need to Know" Authorizations in Medical Computer Systems: Responding to the Constitutional Requirements, 1994, JAMIA, Proceedings of the Eighteeenth Annual Symposium on Computer Applications in Medical Care, pp. 392-396.*

Wikipedia, the free encyclopedia, Screenshot, May 22, 2009.*

About.com, TechSmith SnagIt 8 Screen Capture Utility for Windows, Apr. 1, 2008.*

Wikipedia, the free encyclopedia, Metadata, May 29, 2009.*

Wikipedia, the free encyclopedia, HUD (video gaming), Dec. 6, 2009.*

Benjamin Wulfe, "Using NET: Deliver the Power of Spy++ to Windows Forms With Our New Tool," from the World Wide Web, mdsn.microsoft.com/.../cc163617.aspx, printed Mar. 19, 2010.

Richard King et al., "A novel method of accurately calculating the radiographic magnification of the hip," Warwick Orthopaedics, 2009.

OrthoView, "Joint Replacement," from the World Wide Web, C:/.../Joint Replacement—OrthoView.h . . . , printed on Mar. 19, 2010.

Wikipedia, "Photogrammetry," from the World Wide Web, en.wikipedia.org/wiki/Photogrammetry, printed on Jul. 7, 2010.

Project SIKULI, http://groups,csail.mit.edu/uid/sikuli/, printed from the World Wide Web on Jul. 8, 2010.

EP Application No. 11 17 2626, European Search Report mailed Nov. 10, 2011.

Yusof et al., "Development of Total Knee Replacement Digital Templating Software," Visual Informatics: Bridging Research and Practice, Springer Berlin Heidelberg, Berlin, Heidelberg, pp. 180-190 (Nov. 11, 2009).

Anonymous, "Iconico Screen Calipers," Jan. 2, 2010, 16 pages, Retrieved from the Internet: URL: http://web.archiv.org/web/20100102043404/http://iconico.com/caliper/index.aspx [retrieved on Oct. 20, 2011].

Steinberg et al., "Preoperative planning of total hip replacement using the TraumaCad™ system," Archives of Orthopaedic and Trauma Surgery: Including Arthroscopy and Sports Medicine, vol. 130, No. 12, pp. 1429-1432 (Jan. 13, 2010).

TraumaCad Touch New! and TraumaCad OrthoWeb, Voyant Health, 2 pages, MK200197_B (Dec. 2009).

TraumaCad Touch Guide, BrainLAB's Digital Llghtbox, Orthocrat, www.orthocrat.com, 12 pages.

"TraumaCad User's Guide Version 2.2," Voyant Health, A Voyant Health Ltd. Document, 206 pages (2010).

S. Azrulhizam, S. Riza, K.H., Mohammad and M.K., Abdul Yazid and S. Abdullah, "Scaling Technique for Digital Implant in Medical Images Using Pixel Density Algorithm", European Journal of Scientific Research, 47 (1 ), 24-32 (2010).

Genesis Digital Imaging, "Orthopedic Digital Pre-Operative Planning & Templating Solution" (2009).

H. Handels, J. Ehrhardt, W. Plotz, S.J. Poppl, "Three-dimensional Planning and Simulation of Hip Operations and Computer-Assisted Construction of Endoprostheses in Bone Tumor Surgery" (Jun. 1999).

Y. Kosashvili, N. Shasha, E. Olschewski, 0. Safir, L. White, A. Gross and D. Backstein, "Digital versus conventional templating techniques in preoperative planning for total hip arthroplasty," Can J Surgery, 52(1): 6-11 (2009).

Mascovich, T. and Hughes, J.F., Multi-finger cursor techniques; Proc. GI '06, Toronto: CIPS, 1-7 (2006).

Monika Michalfkova, Lucia Bednarcfkova, Martin Petrfk, Jozef Zivcak, Richard Rasi, "The Digital Pre-Operative Planning of Total Hip Arthroplasty", Acta Polytechnica Hungarica, vol. 7, No. 3 (2010).

William J. Murzic, Zeev Glozman, and Paula Lowe, "Digital Templating in Total Hip Replacement", US Musculoskeletal Review (2006).

* cited by examiner

METHOD AND DEVICE FOR DIGITAL IMAGE TEMPLATING

BACKGROUND

Orthopedic joint replacement and stabilization surgery has grown in popularity over the course of the last several decades. Advances in technology have made procedures such as hip replacement, knee replacement, and bone stabilization commonplace. Joint replacement procedures typically involve replacing a damaged joint with a prosthetic implant that is shaped in a way that allows movement similar to that of a healthy joint. Stabilization procedures typically involve bracing or fixating an injured bone so that it heals properly. Implants used in both types of procedures may be made from metal, plastic, ceramic, or some other substance.

In order for an orthopedic replacement procedure to be successful, a physician must be able to anticipate both the type and size of implant needed. Doing so reduces the risk of complications during the procedure, including nerve injury, instability, intraoperative fracture while inserting the implant, postoperative pain, and even failure to have the correct hardware available. Use of a proper implant also enables the procedure to be performed safely and accurately, providing strong fixation between implant and bone. Thus, being able to anticipate both the type and size of the implant is desirable to ensure the procedure's success.

Traditionally, a physician would manually size implants to radiographic (i.e., x-ray) images of the patient's joint and the associated bone structure. The physician would place a clear sheet, or template, containing an outline in the shape of the implant over the radiograph. This outline may include points, solid lines, dashed lines, or dotted lines, at least some of which may correspond to common bone structure or physiological reference points. Given that radiographic images are typically magnified by approximately 10% to 25%, the template is also typically magnified to account for the anticipated magnification of the patient's bone structure when a radiograph is taken.

The physician could then line up the template to a section of the patient's bone structure. By using multiple templates of different sizes in essentially a trial-and-error procedure, the physician would eventually determine a size for the actual implant hardware. However, this method is often inaccurate due to an inherent weakness. Traditional templates can only provide one magnification. As a result, it is usually an average for the entire population. Yet, magnification in the general population varies widely as it is proportional to body habitus. For example, extremely large patients have much greater magnification on their radiographs than small patients. As a result, this traditional procedure is subject to the risk that an implant of the wrong size will be used.

In order to overcome this problem, some physicians place a sizing marker on the radiograph which enables them to more accurately determine the magnification of the radiograph. Once the radiograph has been templated, the physician then adjusts the final result by the determined magnification. This method ultimately fails because the template is not resized to the correct magnification before being placed over the radiograph. As a result, the incorrectly sized template is placed in the incorrect position. Unfortunately, any template in the incorrect position cannot accurately determine the size of implant hardware needed. Therefore, using a magnification marker for traditional templating does not improve the accuracy of the templating process.

To improve the accuracy of traditional templating, many physicians now use digital templating. With digital templating, the physician views the radiographic image on a computer, and uses a computer representation of the template to attempt to fit the template to the bone to be replaced or stabilized. Digital templating has a significant advantage over traditional methods in that digital templates are not limited to one size magnification. Templating software enables either the templates or the radiograph to be adjusted to the correct magnification prior to placement of the template. Nonetheless, while digital templating addresses some of the problems of orthopedic templating, current systems have several disadvantages, in that they are proprietary, inflexible, prohibitively expensive, difficult to set up and maintain, and hard to use.

OVERVIEW

The embodiments herein are generally directed to reducing the cost of digital image templating while improving its ease of use. In particular, a digital representation of a radiograph may be viewed on a computer screen. The radiograph may depict a reference object of a known size and a bone structure. The magnification level of the radiograph may be unknown. Therefore, in order to determine a properly-sized orthopedic implant, the magnification level of the radiograph should be determined so that the actual physical size of the bone structure can be ascertained.

Preferably independent of the application being used to view the radiograph, a templating application may be executed and displayed on at least part of the computer screen. The templating application may transparently or semi-transparently overlay the radiograph viewing application, thereby allowing a user (e.g., a physician, physician's assistant, technician, nurse, sales representative, etc.) to simultaneously view output from both applications.

The templating application may measure the size of the reference object to determine the magnification level of the radiographic image. For instance, if the reference object is a disc or ball with a 25 millimeter diameter, measuring the size of the disc or ball as it appears on the computer screen can be used to determine the actual size of the bone structure.

Then, from the templating application, the user may select a template of an implant type (e.g., a hip or knee joint) to match the bone structure displayed in the radiograph. Further, the user may select an implant size from one of potentially several discrete ranges of implant sizes. The chosen template may be displayed on the computer screen scaled to match the magnification level of the radiograph. In this way, the user can rotate and move the template on the radiographic image until the template substantially matches the section of the bone structure that the implant is intended to replace or stabilize. If the user finds that the chosen template is not a good match for the bone structure, the user may select a template of a different type or size from the discrete range of implant sizes, and attempt to match this template to the bone structure. The user may continue this process until a properly-sized template is found. Alternatively, the templating application may suggest, recommend, or choose sizes for the user. For some orthopedic procedures, multiple templates may be selected, sized, and matched to the bone structure one at a time or simultaneously.

Accordingly, in an example embodiment, a computing device may facilitate or undertake substantially matching a template object (e.g., a representation of an implant) to a target object (e.g., a bone structure). Preferably, the template object represents at least a section of the target object. The target object may be displayed in a radiograph, along with a reference object of known size.

From the known size of the reference object, the computing device may determine the magnification level, or scale, at which the target object and reference object are represented. Then, the computing device may adjust at least one of the template object and the target object so that the template object substantially matches at least the represented section of the target object. If the template object is adjusted, the initial size of the template object may be chosen from a discrete range of sizes, and the final size of the template object may be based on applying the scale to the initial size.

The computing device may also overlay the template object and the target object. To do so, the template object, the target object, or both may be displayed in a transparent or semi-transparent fashion so that both the template object and the target object are visible. The computing device may also rotate or move the template object to substantially align the template object with at least the matched part of the target object. The alignment may occur automatically or with the guidance of a user.

Advantageously, the computer application, or program, that displays the reference object and the target object may be different from the computer application that displays and sizes the template object. These two applications may be independent of one another, not sharing program instructions or memory. Further, these two applications might not communicate with one another. Thus, the application that displays the reference object and the target object may be an image viewing application, and the application that displays and sizes the template object may be a templating application.

This independent arrangement may serve to simplify the hardware or software architecture of the digital templating system. The image viewing application can be any type of application, including but not limited to, a traditional image viewer such as ADOBE PHOTOSHOP®, a specialized medical image viewer, an email client, or a web browser. The templating application may independently execute in the foreground or background on the same computing device. Thus, the templating application can operate with any application that displays the reference object and the target object, and neither this application nor the templating application are burdened by the effort and complexity of integrating the functions of one into the other.

Further, the templating application does not need to be integrated into existing medical imaging software as a module or plug-in, nor does the templating application need to be integrated within the security infrastructure of complex computer networks that span multiple hospitals, physician's offices, and imaging centers.

Despite the focus of the example embodiments herein, these embodiments also are not limited to orthopedics in general. In addition to the uses described above, the present invention can be used in fields such as architecture, space planning, and civil engineering, or any other field where a template is matched to features depicted in an image. Moreover, the methods and devices disclosed herein may operate on or make use of a wide range of physical or logical computer hardware components, and may be implemented on any type of software platform.

These and other aspects and advantages will become apparent to those of ordinary skill in the art by reading the following detailed description, with reference where appropriate to the accompanying drawings. Further, it should be understood that the foregoing overview is merely for purposes of example and is not intended to limit the scope of the invention as claimed.

DESCRIPTION

I. Network Architecture and Devices

Disclosed herein are methods and devices for digital image templating. On a computer screen, a template object representing an orthopedic implant may be overlaid on or with a digital representation of a radiograph. The radiograph may depict a bone structure. The template object or the representation of the radiograph may then be scaled, rotated, moved, twisted, bent, or otherwise manipulated until the template object substantially matches the size and alignment of at least a section of the bone structure.

Figure 1:
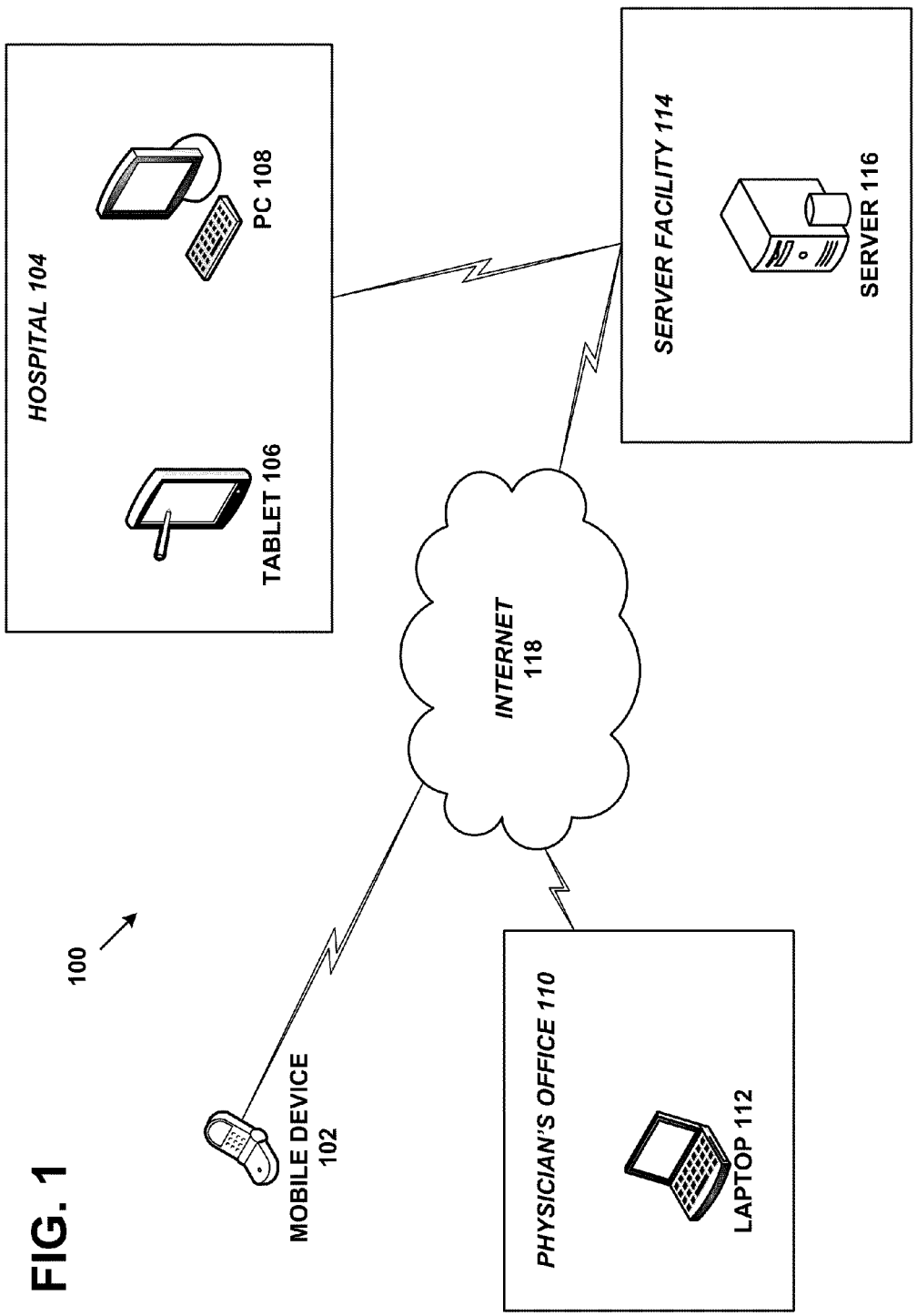
FIG. 1 depicts a number of computing devices, arranged in several physical locations, in accordance with an example embodiment.

FIG. 1 depicts a computing system 100. At a high level, the computing system 100 comprises multiple client devices in multiple physical locations accessing data at a server facility 114. As one example, a mobile device 102, such as a cell phone, communicates wirelessly with the Internet 118 and, in turn, with the server facility 114. In another example, a tablet device 106 and a personal computer (PC) 108 at a hospital 104 communicate using wireless or wireline technologies via the Internet 118 and, in turn, with the server facility 114. In yet another example, a laptop 112 at a physician's office 110 also communicates using wireless or wireline technologies via the Internet 118 and, in turn, with the server facility 114.

Preferably, the server facility 114 contains at least a server device 116 with access to an image database. The images in the database may include depictions of radiographs, indexed by patient, by medical procedure, or by some other means. By centralizing the image database, users of the radiographs, such as physicians, nurses, technicians, and other medical professionals at the hospital 104 and the physician's office 110, can gain access to the radiographs without having to store them locally.

In order to transmit this potentially sensitive medical information over the Internet 118, there may be secure connections (e.g., virtual private networks (VPNs) or Secure Sockets Layer (SSL) connections) between the hospital 104 and the server facility 114, as well as between the physician's office 110 and the server facility 114. Alternatively, these VPNs may be between the individual client devices (i.e., the mobile device 102, the table device 106, the PC 108, and the laptop 112) and the server facility 114, or between the individual client devices and the server 116. Thus, as one example, the mobile device 102 may access the server facility 114 via an Internet Protocol Security (IPSec) VPN or some other form of secure connection.

The communication system 110 is intended to be illustrative rather than limiting. Thus, the server facility 114 may be accessed by more or fewer devices from more or fewer physical locations (for instance, a physician may view these images from a hotel room or his or her residence). Thus, there may be thousands of client devices of various types accessing the images from hundreds of locations. Further, the server facility need not be present in a separate physical location. Instead, the server facility may be integrated into one or more of the physical locations of the client devices. Alternatively or additionally, the functions of the server facility may be integrated into the client devices themselves. Moreover, the Internet may be replaced with a private network or may be omitted altogether.

It should be understood that each device depicted in FIG. 1 may be logically or physical distributed over multiple devices of the same type or of a different type. For instance, functions of the server 116 may be distributed across a plurality of server devices, including, but not limited to databases, processing engines, load balancers, and so on. Each of these server devices may be standard PC or server hardware, or customized PC or server hardware. For example, the server 116 may be a rack-mounted or blade server device.

Figure 2:
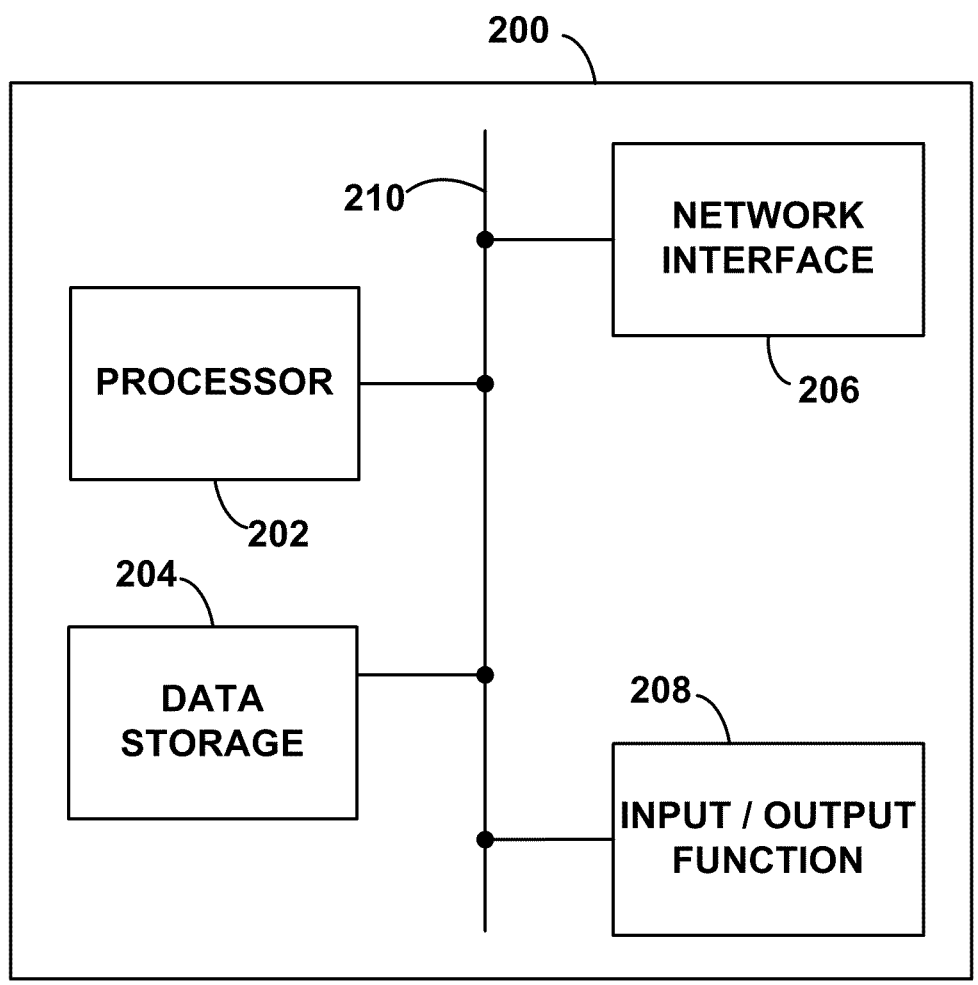
FIG. 2 depicts a block diagram of a computing device that can be used to conduct digital image templating, in accordance with an example embodiment.

FIG. 2 is a simplified block diagram exemplifying the implementation of a device 200 that could be any of the mobile device 102, the tablet device 106, the PC 108, and the laptop 112. FIG. 2 illustrates some of the functional components that would likely be found in such a device arranged to operate in accordance with the embodiments herein.

The device 200 preferably includes a processor 202, a data storage 204, a network interface 206, and an input/output function 208, all of which may be coupled by a system bus 210 or a similar mechanism. The processor 202 preferably includes one or more central processing units (CPUs), such as one or more general purpose processors or one or more dedicated processors (e.g., application specific integrated circuits (ASICs) or digital signal processors (DSPs), etc.) The data storage 204, in turn, may comprise volatile or non-volatile data storage and can be integrated in whole or in part with the processor 202.

The data storage 204 preferably holds program instructions, executable by the processor 202, and data that is manipulated by these instructions, to carry out the various methods, processes, or functions described this specification or the accompanying drawings. Alternatively, these methods, processes, or functions can be defined by hardware, firmware, or any combination of hardware, firmware and software.

The network interface 206 may take the form of a wireline interface, such as an Ethernet, Token Ring, or T-carrier interface. The network interface 206 may also take the form of a wireless interface, such as IEEE 802.11 (Wifi), BLUETOOTH®, or a wide-area wireless interface (e.g., a cellular radio). However, other forms of physical layer connections and other types of standard or proprietary communication protocols may be used over network interface 206. Furthermore, network interface 206 may comprise multiple physical interfaces.

The input/output function 208 may facilitate user interaction with the device 200. Thus, the input/output function 208 may comprise multiple types of input devices, such as a keyboard, a mouse, a touch screen, and so on. Similarly, the input/output function 208 may comprise multiple types of output devices, such as a monitor, printer, or one or more light emitting diodes (LEDs). Additionally or alternatively, the device 200 may support remote access from another device, via network interface 206 or via another interface (not shown), such a universal serial bus (USB) port.

In combination with, in addition to, or as an alternative to the simplified representation of a computing device found in FIG. 2, any of the methods processes, or functions disclosed in this specification or the accompanying drawings may be represented as program instructions on any appropriate computer-readable medium. Thus, embodiments of this invention encompass an article of manufacture, including a non-transitory computer-readable medium, having program instructions stored thereon that, in response to execution by a computing device, cause the computing device to perform operations comprising any of these methods, processes, or functions.

II. Traditional Templating

Figure 3A:
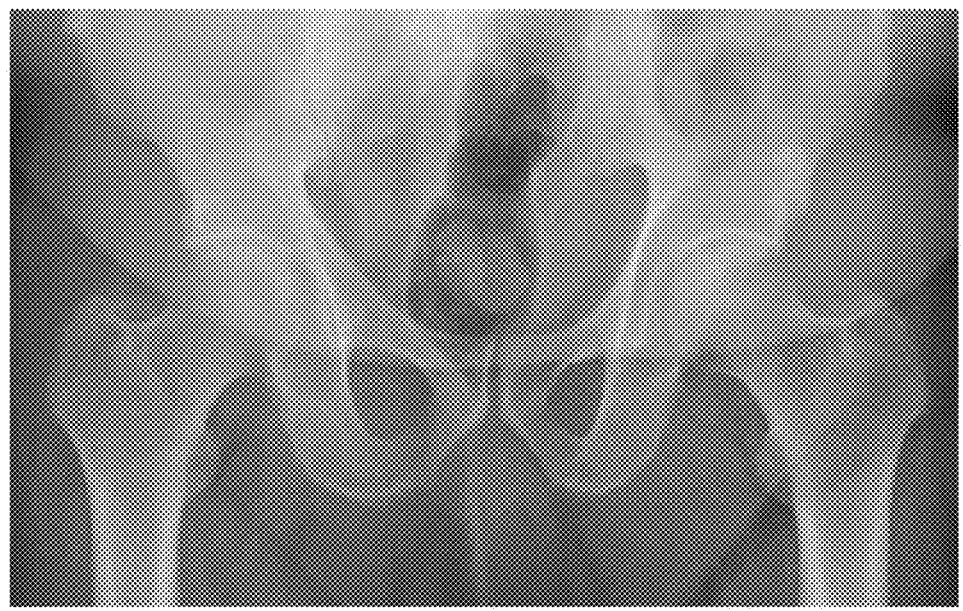
FIG. 3A depicts the display of a radiograph containing a hip bone structure, in accordance with an example embodiment.
Figure 3B:
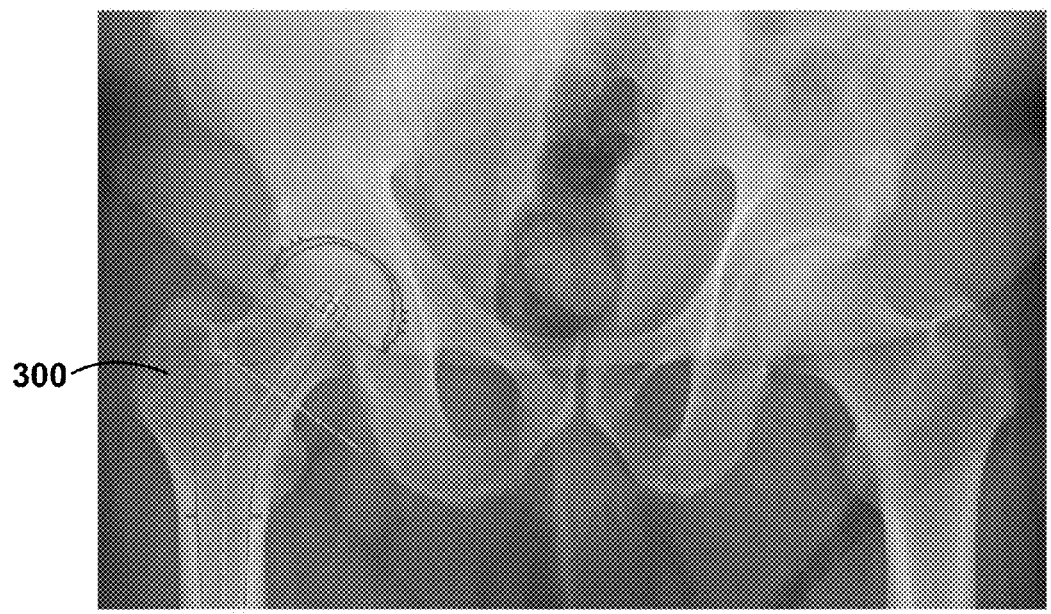
FIG. 3B depicts the display of the radiograph containing a hip bone structure, along with a template of an implant matched to a hip joint to be replaced, in accordance with an example embodiment.

Prior to the widespread use of computers in medicine, implant templating was performed manually. Manual templating typically involves a physician viewing a radiographic film via a projector or placing the radiographic film over a light box so that the radiographic image on the film is illuminated. As shown in FIG. 3A, this illumination may allow the physician to view the bone structure (in this case, a hip) depicted in the radiograph. The physician would also have available a set of clear plastic templates representing implants of various sizes. Each template may represent a particular section of the bone structure. As shown in FIG. 3B, by placing these templates on top of the radiograph, the physician may be able to determine the approximate size of an implant to use with the patient. The physician may rotate or move the template with respect to the radiograph until the physician is satisfied that the template is both of the proper size and aligned with the section of the bone structure it represents.

Templates are typically provided by the manufacturers of implant hardware. Thus, the sizes of the templates may have a one-to-one correspondence with the sizes of implant hardware made by the vendor. Therefore, if a given vendor offers implants in five different sizes, the vendor may also provide templates corresponding to those same five sizes. Each template may represent not only a section of the bone structure (e.g., a joint), but also may include other lines, reference points, markings, or points of attachment that assist the physician in aligning the template with the section of the bone structure.

For example, in FIG. 3B, a physician may arrange a hip joint template with a hip joint depicted in a radiograph until the physician is satisfied with the fit of the template. If the physician is not satisfied with the fit, the physician may choose a template of another size or a template from a different vendor, and repeat the process.

One of the difficulties in traditional templating is that the images depicted in radiographs may be magnified. When a radiograph is taken, an x-ray beam passes through the patient and onto the radiographic film, to produce an image of the patient's bone structure. However, the image of the bone structure may not be equal to the size of the patient's bone, as the image may be magnified. The bone structure's magnification may be proportional to the distance that the bone structure is from the film. As such, if the patient is thin, the bone structure may be closer to the film and the magnification may be small. Conversely, if the patient is muscular or obese, the magnification may be large since the bone may be further from the film. Since there is tremendous variation in human body sizes and shapes, there are correspondingly large variations of magnifications.

In the traditional method of templating, a single set of templates is usually supplied. The templates in the set are based on an estimated average of the magnification in all individuals, since the manufacturer cannot account for all of the variations in image magnification. Thus, the further a patient's body type differs from the estimated average, the templates become more and more inaccurate. Accordingly, orthopedic procedures performed on these patients may have a greater likelihood of complications, since the surgeon, assistant, or sales representative cannot adequately determine what size or type of implant is required. These complications include failure to have the correct hardware at the procedure, intraoperative fracture of bone, failure of the hardware, neurologic injury, chronic pain, or the need for repeat surgery.

In order to overcome this problem, some physicians may place a sizing marker on the radiograph near or at the level of the bone. The marker is preferably of a known size and made from a substance that is visible on radiographs. Using such a radiographic marker enables physicians to more accurately determine the magnification of the bone structure.

However, there are disadvantages to using radiographic markers to assist templating. Although having the radiographic marker in the radiographic image may help the physician determine the magnification level of the bone structure, the physician may not have templates that correspond to this magnification level. Since templating manufacturers cannot account for all the variations in human body habitus and resulting magnifications thereof, surgeons may not have access to the correctly magnified template for each patient. For example, even if a surgeon determines that the magnification of a patient's bone structure is 37%, there will be no template that the surgeon could use to template that bone structure if the templates in the sets are magnified only at 10%, 15%, or 25%.

As a result, some physicians may place an incorrectly magnified template over the bone structure and then adjust the final result by the determined magnification level of the radiograph. However, this method may ultimately fail because the wrong-sized template is used. If the template is not at substantially the same magnification level as the radiograph, it is unlikely that the template can be correctly positioned over the bone structure. If the template is incorrectly positioned over the bone structure, the template cannot be used to adequately determine the final size of the implant. Therefore, using a radiographic marker with traditional templating may not improve the accuracy of the templating process nor reduce the rate of complications.

III. Digital Templating

In order to overcome at least some of the inadequacies of traditional templating, digital templating can be employed. Generally speaking, digital templating involves a digital image of a radiograph depicting a bone structure being shown on a computer screen, along with a digital representation of a template. Via a computer interface, a physician may be able to size, rotate, or move the representation of the template so that it is aligned with the at least a section of the bone structure. In this way, the physician is able to perform orthopedic templating from virtually any computer device.

To that point, the communication system 100 of FIG. 1 is a suitable architecture for digital templating. In particular, many medical imaging systems use the Picture Archiving and Communication System (PACS) hardware and software. PACS is designed for storage, management, and access to digital images, and is used primarily by the medical community. Thus, many medical devices, such as magnetic resonance imaging (MRI), ultrasound, and x-ray machines are integrated to some extent with PACS. PACS uses the Digital Imaging and Communications in Medicine (DICOM) format for the storage and communication of these images. A goal of standardizing upon PACS and DICOM is to allow medical professionals to be able to securely store, view, and share digital images. For instance the server 116 could be a PACS server, and each of the client devices may include PACS client software.

Given the trend in recent years toward digital imaging in the medical profession, PACS use has become widespread to the point that it is virtually required in some practices. In response to this demand, many hardware and software vendors have developed PACS compatible devices and applications. For instance, there are a wide variety of PACS clients available for PCs running MICROSOFT® or APPLE® operating systems.

However, while using a system like PACS has advantages, doing so also has significant shortcomings. PACS systems can be prohibitively expensive. For instance, a physician in a small or medium sized practice may be reluctant to spend the initial capital required to install PACS hardware or software in the practice. Additionally, the PACS vendor may also charge regular maintenance or service fees for access to the PACS server. Further, due to PACS clients typically being in communication with PACS servers via the Internet, the transfer and manipulation of large images can be slow, and slow response times can lead to user frustration.

Moreover, physicians tend to be busy professionals, and may not have much computer experience. Thus, as a general rule, physicians want their computer applications to "just work." As a result, they may not have the patience to learn the full capabilities of a PACS client user interface, especially since these physicians are likely to already be comfortable with manual methods of orthopedic templating. Further, as the physician moves between client devices that use different PACS client software, the physician may not want to have to learn multiple user interfaces. Even if the physician is comfortable with using more than one PACS client, each PACS client may require configuration of a VPN to a different PACS server facility. For small practices, the physicians and their staff may not have the information technology (IT) expertise to set up these VPNs, and may not have the budget to hire part or full time IT professionals to configure and maintain VPNs.

Another disadvantage to using PACS clients for digital templating is that it has proven difficult for implant vendors to integrate their templates into PACS client software packages. Implant vendors and PACS client software vendors may be different entities. Thus, in order for an implant vendor to have their implants included in multiple PACS client software packages, the implant vendor may have to reach business arrangements with each of the PACS software vendors. Even if the implant vendor is able make these arrangements, the implant vendor would still have to integrate their templating specifications into the potentially disparate software architectures of each PACS client. As a result of this difficulty, implant vendors may support only their own proprietary PACS clients. Consequently, physicians may need to use multiple PACS clients in order to perform digital templating, leading to additional cost and frustration.

Typically, templating software is implemented into PACS in several ways. Using one method, a templating software vendor may integrate the templating software within their proprietary PACS software clients. The templating software can only be used with their proprietary PACS client and requires the user to purchase their PACS solution including the hardware and software, in addition to the templating software. This can be prohibitively expensive and require physicians to repurchase an entirely new system including PACS hardware, PACS software, and templating software just to be able to perform templating. Furthermore, the physician may be "locked" into the vendor's system and cannot choose "best-of-breed" components or modules without changing to or purchasing an expensive new system.

Other vendors offer a solution to this problem. Some templating vendors specialize in integrating templating within other PACS vendors' software. In this fashion, they can offer templating to those physician practices that already have an established PACS system. This potentially eliminates the need for the practice to invest in an entirely new system. However, this method also has significant drawbacks, as integration with each separate PACS vendor's proprietary software is both time-consuming and expensive for the templating vendor, and this significant cost is passed onto the physician's practice. Furthermore, changes in the proprietary PACS systems of the physician require a corresponding update in the templating software with expensive reprogramming. Moreover, templating vendors are unlikely to be able to integrate within all proprietary PACS systems as there are literally hundreds of systems.

Another option may be offered by templating vendors. In order to eliminate the time consuming and costly integration of their software within proprietary PACS software, they will integrate their own templating software within their own proprietary PACS client. This PACS client is then integrated within users' existing PACS network either locally or as a server that can be accessed via an Internet connection.

Nonetheless, there are several problems with this solution. In particular, it requires that users learn two different PACS clients—one for day-to-day use and another for templating. As these PACS clients are complex, the user may effectively have to re-learn the templating application with each use. This is especially frustrating for users that are used to the relative simplicity of traditional templating. Additionally, requiring an Internet-based solution can lead to the templating application to respond slowly when there is network congestion, and potentially to be unavailable when network connectivity is down.

Moreover, this method only moved costs, it did not decrease costs. Although costs associated with PACS software integration may have been eliminated, costly network integration and support may be required. The templating vendor must now work to integrate their system into the multiple complex networks used by physicians. For example, a typical orthopedic physician works at multiple hospitals and surgery centers, each with their own information technology department and unique network and VPN security settings. The physician also has their unique network which may include more than one office, an imaging unit, and a surgery center. The templating vendor must work with the physician's information technology department to integrate within this network as well. This may be time consuming and expensive, and this cost may be passed onto the physician. Unfortunately, the costs do not end there, as the templating vendor may require costly annual maintenance fees to support this network and integration. For example, any time the PACS network or VPN settings change, the templating software could require a corresponding change, resulting in maintenance work by the vendor.

Figure 4:
FIG. 4 depicts the display of a radiograph via an image viewing application, as well as the display of a user interface of a templating application, in accordance with an example embodiment.

FIG. 4 depicts an embodiment that addresses both these technical and business obstacles. In particular, FIG. 4 includes a digitally-displayed radiograph 400 of a knee bone structure. The application that displays the radiograph 400 may be, for instance, a PACS client, or some other type of image viewer. In addition to the bone structure, the radiograph may also display a radiographic marker 404. On top or alongside the display of radiograph 400, the user interface of a templating application 402 may be displayed.

Preferably, the templating application is independent of the application that displays the radiograph 400. This independence could be exhibited in a number of ways. For instance, these two applications could take the form of two different executable files that were separately compiled. As such, these applications might not share memory or code with one another. Further, these applications might not communicate with one another. However, it is well-known in the art that two applications can share common object code or library code, such as dynamically-linked libraries (DLLs) or other forms of shared libraries, without losing their independence from one another.

In an optional embodiment, the templating application may perform or trigger a screen capture operation of the display of the radiograph 400. It should be understood that a screen capture operation may cause an image of this display to be recorded. Thus, for instance, the templating application may make a copy of some or all parts of the output on the computer screen. Then, the templating application may read, use, or manipulate this copy when performing templating functions. Doing so allows a further degree of independence between the templating application and the application that displays the radiograph 400. Particularly, once the screen capture is performed, the radiograph 400 can be resized, moved, closed, or deleted without impacting the templating application. This screen capture can be performed upon initiation of the templating application, or at any other time during the course of templating. Nonetheless, performing a screen capture is not a necessary step of templating, and templating can be conducted without performance of screen captures.

In another optional embodiment, the templating application could take the form of a "widget" or a "gadget." For example, a widget for the MAC OS® operating system is an application that is not displayed to the user until the user activates the widget (e.g., with a keystroke or by some other means). Once activated, the widget may appear in the foreground, either with background applications dimmed, or by transparently or semi-transparently overlaying these applications. An activated widget may be able to be moved, rearranged, de-activated, or deleted. Typically, widgets perform simple tasks such as clock, weather, and calendar functions, but in full generality, widgets can perform any tasks that a standard computer application could perform. Widgets may be associated with some form of dashboard, launcher, or sidebar so that the user has easy access to initiating and using the widget.

Widgets are similar in concept to the gadgets of MICROSOFT WINDOWS VISTA® and WINDOWS 7®, as well as other types of user interface constructs available on other operating systems and graphical user interfaces. Thus, the use of widgets is not confined to such MICROSOFT® or APPLE® operating systems, and may be used with other types of operating systems as well.

The programming environment used to create widgets may be standard or proprietary. For instance, some widgets could be created through use of standard HyperText Markup Language (HTML), Cascading Style Sheets (CSS), or JavaScript. On the other hand proprietary schemes such as ADOBE AIR®, ADOBE® Flash or SILVERLIGHT® could also be used. Of course, the templating application 402 could be based on other tools, platforms, or technologies as well.

Regardless of how it is implemented, the templating application 402 preferably comprises one or more tabs, text boxes, sliders, radio buttons, menus or other user interface components that allow the user to perform at least one of the following functions: (a) measuring the size of the radiographic marker 404 in the radiograph 400, (b) selecting a template that represents an implant of a particular manufacturer and size, or (c) rotating or moving the selected template so that the template and at least a section of the bone structure depicted by the radiograph 400 are overlaid. Of course, the templating application 402 may contain logic, in the form of program instructions, to perform these functions. For example, this logic may perform measurements of simple lengths, diameters, and angles. The logic may also perform more complex measurements requiring a combination of measurements, calculations and comparisons. Further, the templating application 402 may be able to perform additional functions not explicitly discussed herein.

As discussed above, the radiographic marker 404 may be measured. One way of accomplishing this goal is for the templating application 402 to allow the user to specify the location of reference points associated with the radiographic marker 404. For instance, the user may select the radiographic marker 404 with a mouse pointer or a touchscreen input device, and thereby specify its radius, diameter, or outline. In doing so, the templating application 402 may mark this radius, diameter, or outline on the screen with one or more points, lines, or other indicia. Of course, the templating application 402 may include functions for automatically detecting and specifying the radiographic marker 404.

Once the radiographic marker 404 has been specified, its virtual size may be measured. Preferably, the virtual size of an object displayed on a computer screen can be represented by the size of the object as shown on the screen. For instance, if the radiographic marker 404 is 25 millimeters in diameter, but is displayed with a diameter of 50 millimeters, then its magnification level is 100% (the size of the radiographic marker 404 has been doubled). The virtual size of an object can also be measured by the number of pixels used in the geometry of the radiographic marker 404.

As is known in the art, a pixel (a shortened version of the term "picture element") may refer to a dot-like point displayed on two-dimensional grid. Typically, the grid appears on a computer screen. By lighting, or turning on, various pixels with appropriate colors, images can be formed on the computer screen. As or after the templating application 402 marks the radius, diameter, or outline of the radiographic marker 404, the templating application 402 may determine the approximate or exact number of vertical or horizontal pixels in the display of the radiographic marker 404. This number can then be used in various ways to determine the actual size of the bone structure depicted in the radiograph.

For instance, if the radiographic marker 404 is known to be 25 millimeters in diameter, and the templating application determines that there are 75 pixels in the display of the radiographic marker 404, then the templating application 402 has also determined that the radiograph depicts the image at a ratio of three pixels per millimeter. Then, the templating application 402 can shrink or expand the displayed sizes of templates in order to match this ratio. Thus, if a particular implant has an axial length of 300 millimeters, the templating application 402 may display the corresponding template of the implant using 900 pixels to represent the implant's axial length. In this way, the template is displayed at approximately the same scale as the bone structure, resulting in a better matching of the template to the bone structure.

In order to facilitate this functionality, the templating application 402 may contain or have access to one or more a template libraries. Each template library may contain one or more templates from a given implant vendor. Preferably, each implant size for a given piece of implant hardware is represented with a template in the template library. The templating application 402 may allow the user to search for or select a template by medical procedure, implant vendor, or size. In addition to including implants of different sizes, templates of different shapes and designs may also be included in these databases, and these templates may also be chosen by the user. Once a template is chosen and scaled according to the measured size of the reference object, the template may be displayed in conjunction with the bone structure.

Figure 5A:
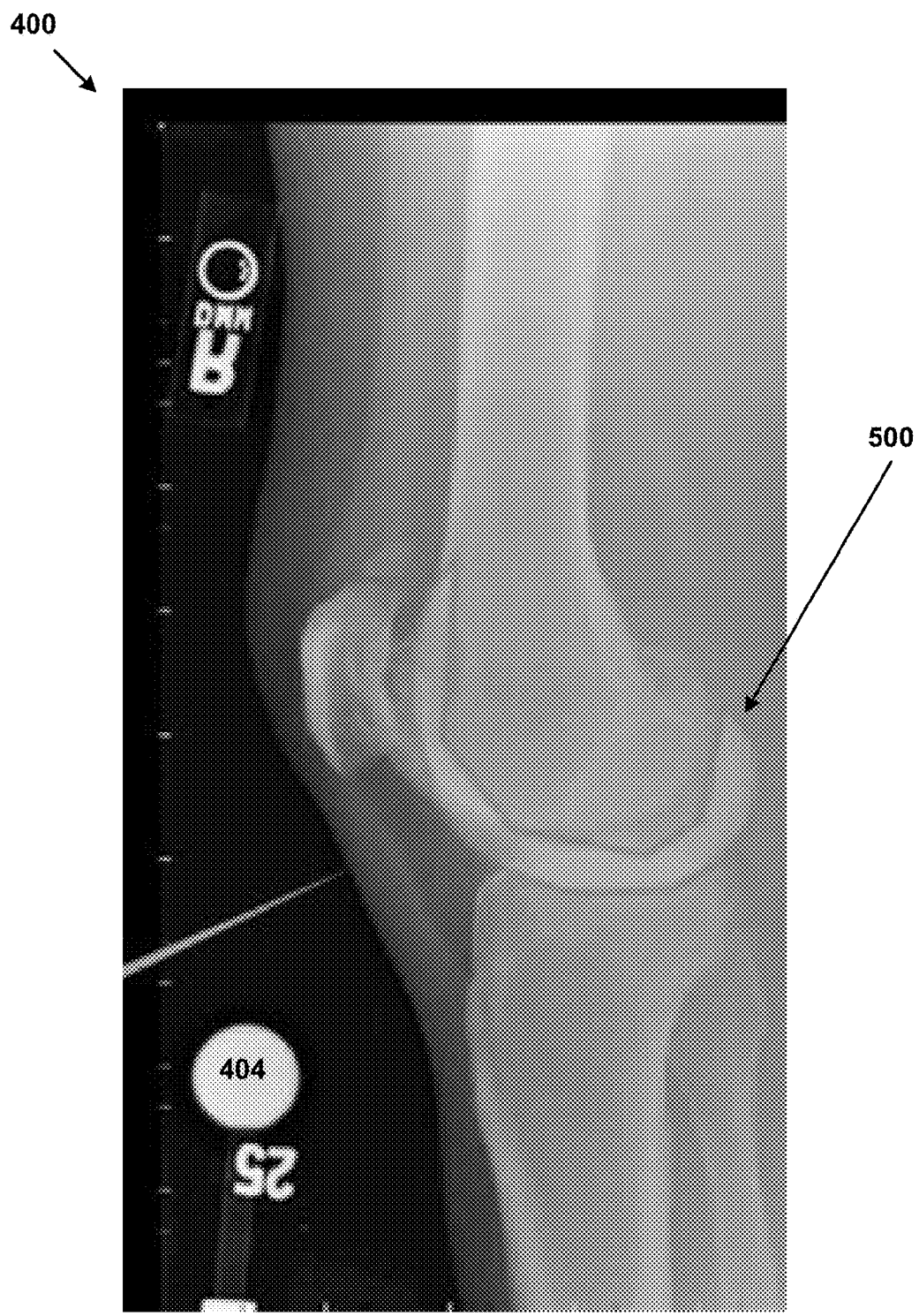
FIG. 5A depicts the fitting of a digital template to a radiographic image of a bone structure, in accordance with an example embodiment.

FIG. 5A depicts the placement of a template 500 on the radiograph 400. In this case, the template 500 represents part of an implant for replacing a knee. As shown in FIG. 5A, the template 500 may be displayed transparently or semi-transparently so that it can be matched to a section of the bone structure. Alternatively, the bone structure may be displayed transparently or semi-transparently instead.

Also as shown in FIG. 5A, the template 500 is not completely in place. Therefore, the templating application 402 (which is not shown in FIG. 5A in order to focus on the fit of the template to the bone structure) may allow the user to rotate or move the template 500 so that the template 500 substantially aligns with at least a section of the bone structure. Alternatively, the templating application 402 may automatically perform rotation or movement on behalf of the user, or may suggest rotation or movement to the user.

Further, in orthopedic procedures to stabilize bone fractures, templates may be used to size plates, rods, screws, or pins that may be attached to or placed within fractured bones. In order to properly align such templates, the templating application may also allow the user to twist or bend the template 500 so that the template 500 substantially aligns with at least a section of the bone structure. In other orthopedic procedures, hardware may also be used to stabilize bone structures following a bone cut. This typically may be done during corrective procedures to improve bone alignment.

In some orthopedic procedures, more than one template may be used. Thus, a similar series of steps to scale, select, rotate, and move each template may be performed. Moreover, the templating application may allow the user to specify how and where these templates may be connected or may interact with one another.

Regardless, once the user is satisfied with the size and alignment of the template 500, the user may indicate as such to the templating application 402, and the templating application 402 may indicate or record characteristics of the template 500 (e.g., the make, model, brand or size of the template 500). Additionally, the templating application 402 may associate these characteristics with the radiographic image 400, or with the patient of whom the radiographic image 400 was taken.

Use of the templating application 402 has a number of advantages over other methods of templating. The templating application 402 does not require the costly and complex integration required with PACS-based templating solutions. Thus, the templating application 402 does not need to be integrated and maintained within proprietary PACs software or within multiple complex networks, significantly reducing both cost and time to implementation.

The templating application 402 also enables the user to select a best-of-breed PACS system that best suits their needs, not just a PACS system that allows the user to perform templating. Additionally, the templating application 402 may prevent the user from having to repurchase an entirely new PACS system. Moreover, the user may modify or upgrade a PACS system without having to worry about costly system upgrades, changes, or downtime due to the PACS system's integration with the templating application 402.

In addition, by performing digital templating with a templating application that is independent from the application that displays the radiograph, the templating application can be used with any such image display application. Thus, templating application 402 could be used not only with any PACS client, but also with email applications, messaging applications, web browsing applications, file transfer applications, or image viewing applications. Further, since a PACS client is not required to perform the templating procedures, a VPN or other form of secure connection need not be in place. Thus, for example, the user of the templating application 402 may receive a radiograph via email and then perform templating with the radiograph as displayed in his or her email client application. With the radiograph stored and manipulated locally on the user's computer, the delays and slowness associated with secure network access and large file size can be avoided. Further, the independence of the templating application 402 from the application that displays the radiograph may also result in users only having to learn one templating application user interface. This may save time and reduce user frustration.

However, any independence of the templating application from the image viewing application does not imply that the templating application cannot communicate with other networked devices. For example, the templating application may send and receive radiographic images from one or more servers that store these images in a centralized or distributed fashion. This arrangement facilitates communication between surgeons, assistants, sales representatives, and so on.

Figure 5B:
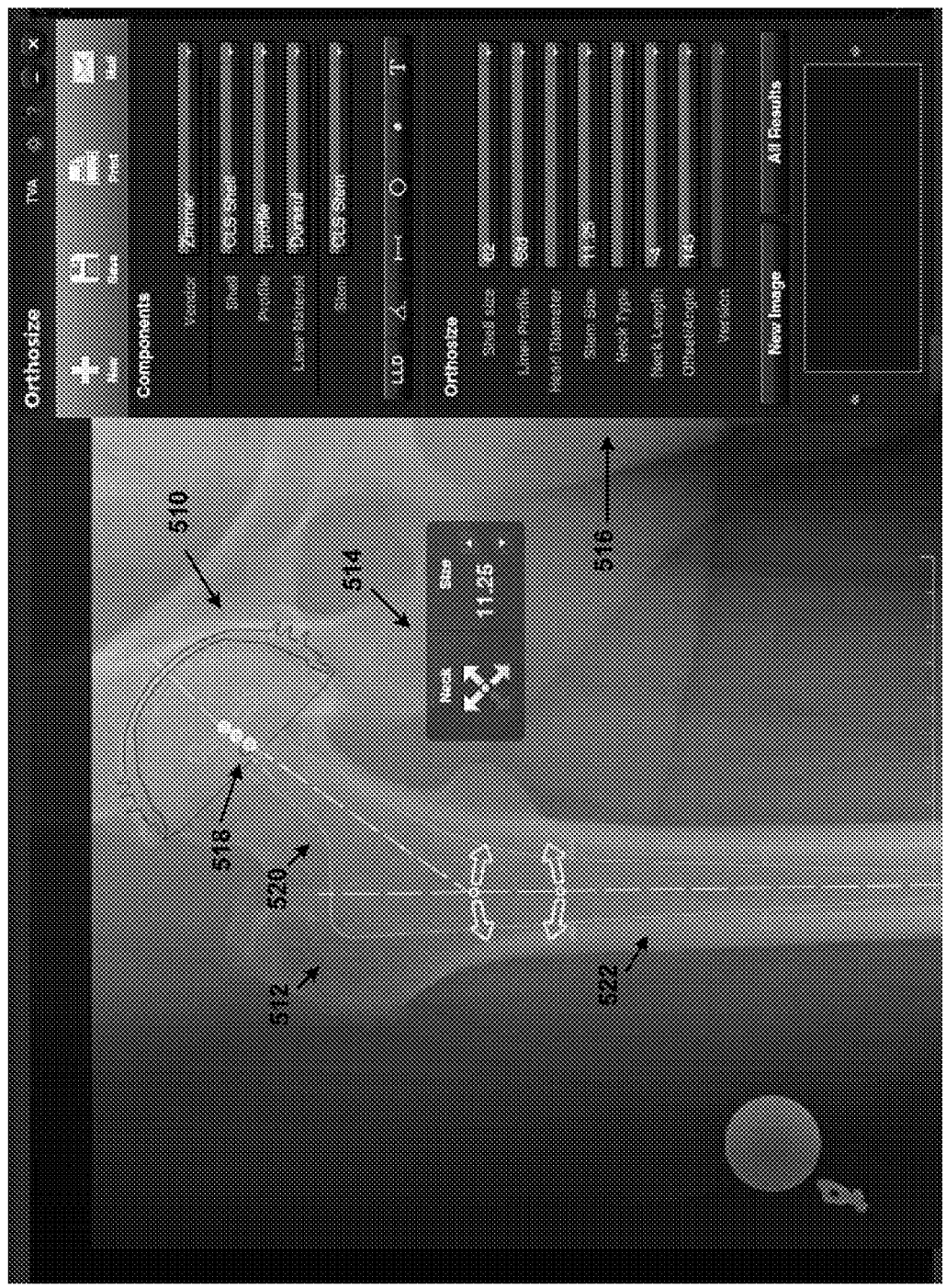
FIG. 5B also depicts the fitting of a digital template to a radiographic image of a bone structure, in accordance with an example embodiment.

FIG. 5B depicts an illustrative graphical user interface design for placement of templates on a radiographic image. Although FIG. 5B shows templating for a hip replacement procedure, the general approach shown in FIG. 5B can be applied to other procedures as well. This optional interface design advantageously allows the manipulation of a shell template 510 and a stem template 512, as well as their relationship with one another, via a heads up display 514. Preferably, the heads up display 514 comprises a form of floating dialog box that appears somewhat near the shell template 510 and the stem template 512. The heads up display 514 may be modeless so that its presence does not block the user from interacting with other parts of the templating application 516 or other applications.

Rather than requiring the user to manipulate each object from one or more drop-down menus (or other types of selection mechanisms) in the templating application 516, the heads up display 514 (which may be considered part of the templating application 516) allows the user to specify the shell template 510 and the stem template 512 via a simplified user interface. In particular, the user may specify the size, length, and offset of the shell template 510. Likewise, the user may manipulate length of the neck 520 and size of the stem 522 of the stem template 512, as well as the stem angle, offset and version. Any size changes may be depicted by the user interface changing the display sizes of the shell template 510 or the stem template 512. Neck length, offset, and version changes may be represented by the connection points 518 for the shell template 510 or the stem template 512. Once these points are positioned either through the use of the heads up display 514 or other user interface components, the computing device may perform several calculations including changes in leg length and offset.

For hip replacement procedures, offset may be defined as the horizontal distance between the final head position of the implant and the shaft of the femur, while leg length may be defined as the vertical distance. This vertical and horizontal distance may be made larger or smaller to optimize postoperative hip biomechanics. The heads up display 514 may allow the user to fine tune the postoperative leg length and offset to prevent postoperative nerve injury, limp, hip instability, and pain. For other types of orthopedic procedures, offset may take on other definitions.

For instance, the user may choose the shell template 510, and then place, size, or align this template on the radiographic image so that the shell template 510 substantially matches the hip socket depicted in the radiographic image. The procedure may also involve the user choosing the stem template 512, and then placing, sizing, and aligning this template on the radiographic image so that the stem template 512 substantially matches the leg bone depicted in the radiographic image. Advantageously, some or all of these steps may be performed via the heads up display 514, so that the user does not need to refer back and forth between the templates and the drop down menus of templating application 516.

The heads up display 514 may also facilitate the positioning of the shell template 510 and the stem template 512 with one another. Such positioning may influence the patient's post-operation leg length and offset. Thus, for instance, the heads up display 514 may allow the user to select the connecting points 518 on either or both of the shell template 510 and the stem template 512. By selecting one of several such points, the alignment of the shell template 510 and the stem template 512 may be chosen to provide a desired leg length or offset.

Of course, any of the procedures shown in FIGS. 5A and 5B are for purposes of example, and are non-limiting. Thus, the embodiments herein may be applied to other types of orthopedic procedures, as well as to non-orthopedic procedures. Further, any of the steps described with respect to these figures may be automated in whole or in part.

IV. Example Embodiments of Digital Templating

Figure 6:
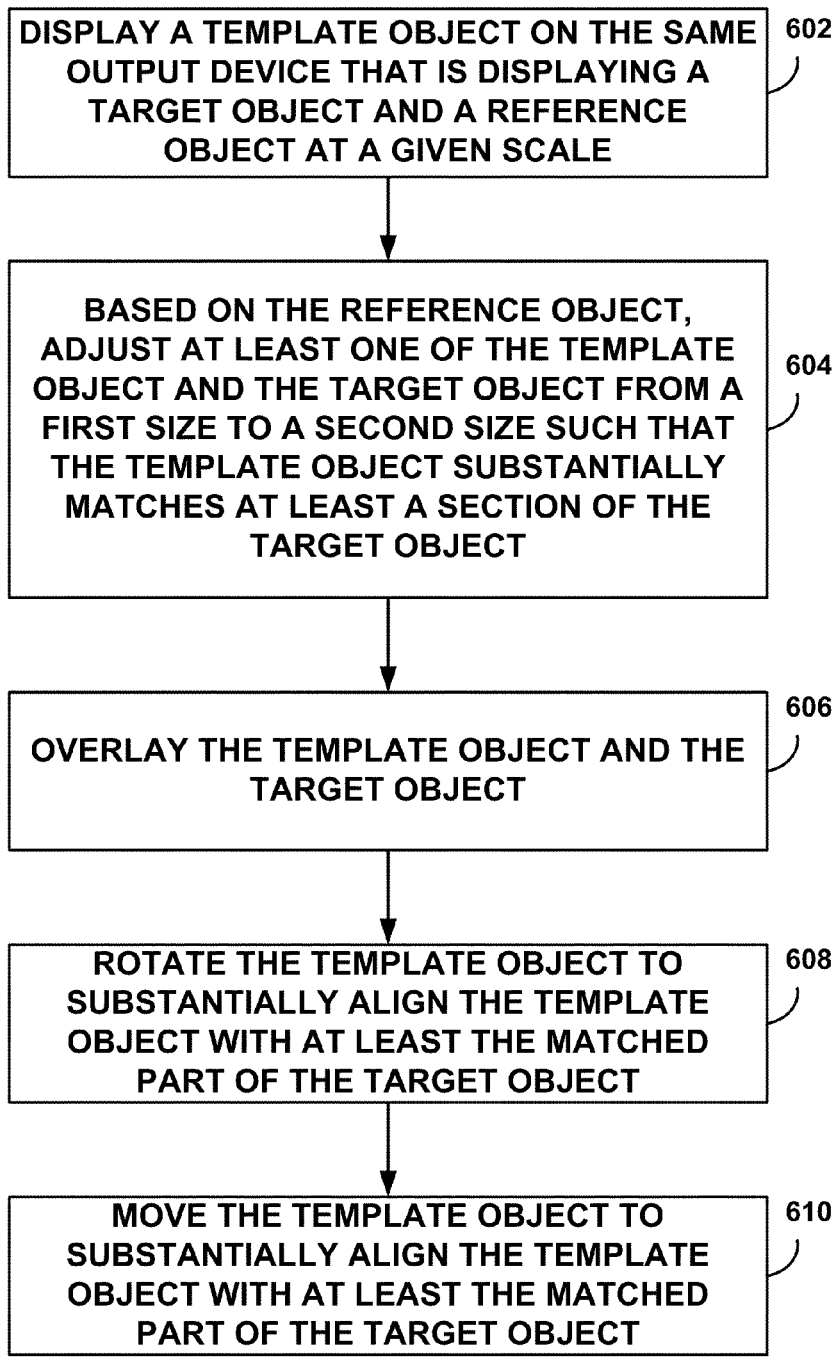
FIG. 6 is a flow chart, in accordance with an example embodiment.
Figure 7:
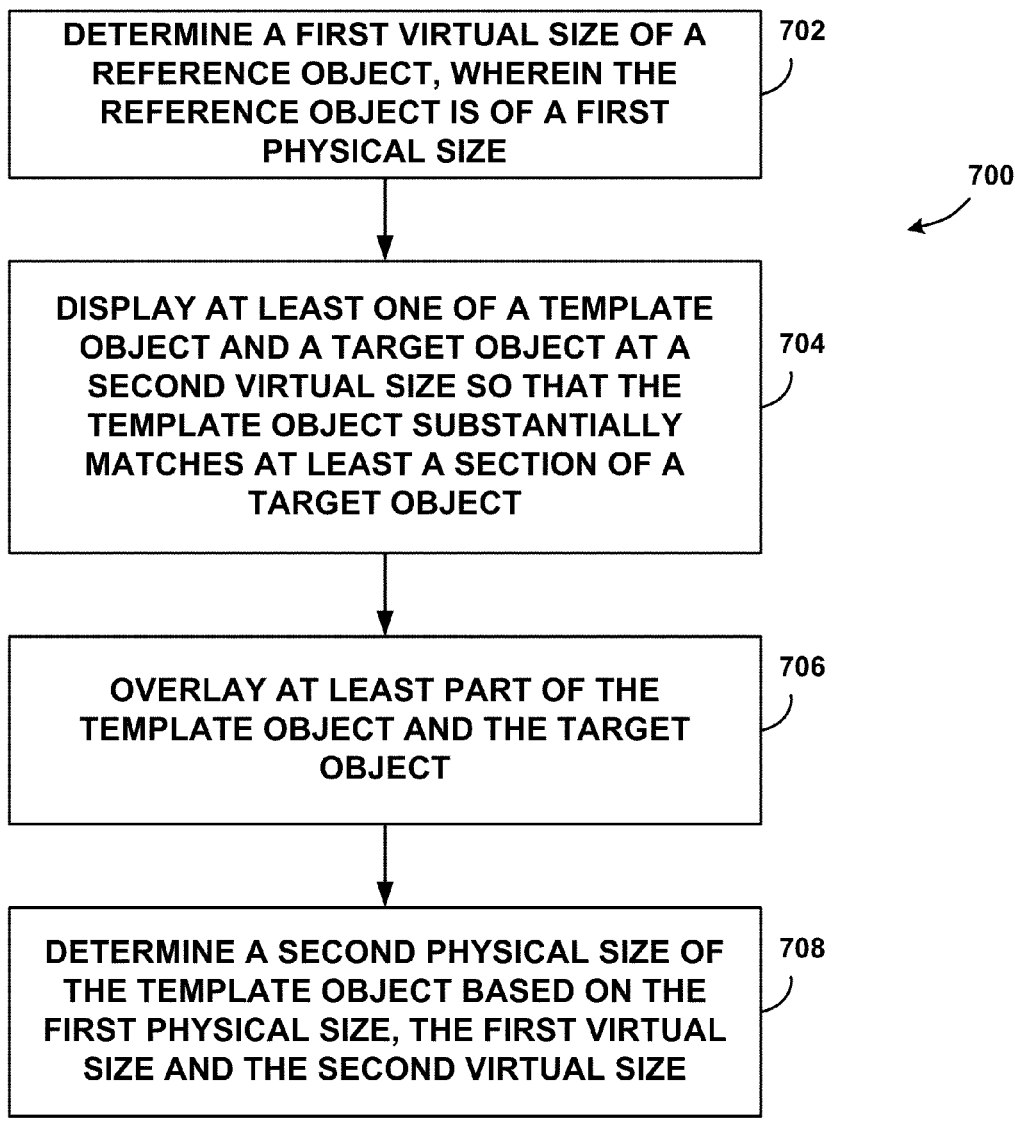
FIG. 7 is another flow chart, in accordance with an example embodiment.

FIGS. 6 and 7 are flow charts 600 and 700, respectively, of example embodiments for digital templating. It should be understood that, for each of these flow charts, more or fewer steps may be used. Thus, for example, steps may be added to or omitted from flow chart 600 or flow chart 700. Further, the ordering of the steps in each flow chart is for purposes of example, and other orders of steps may be used. Additionally, flow charts 600 and 700 may be combined with one another, in whole or in part, without departing from the scope of the invention. Thus, as a whole, it should be understood that these flow charts are intended to be illustrative rather than limiting.

Flow chart 600 is arranged according to an example embodiment. At step 602, a template object is displayed on an output device that is also displaying a target object and a reference object. The target object may depict a radiographic picture of a bone structure, and the template object may represent a replacement part for the bone structure or a stabilization implant for the bone structure. The target object and reference object may be displayed at an initially unknown magnification level, or scale. Preferably, the reference object is of a known size. Thus, by measuring the size of the reference object as displayed, the magnification level can be discovered.

At step 604, based on the measured size of the reference object, at least one of the template object and the target object may be adjusted from a first size to a second size such that the template object substantially matches at least a section of the target object. At step 606, the template object may be overlaid on or with the target object. This overlaying may occur before or after the template object or the target object is adjusted from the first size to the second size. Additionally, the overlaying may involve displaying the template object or the target object in a transparent or semi-transparent fashion.

If the template object is sized, the first size may be chosen from a range of sizes. Each size in this range may correspond to a particular model, brand, or make of implant hardware. Further, the first and second sizes may have any relation to one another. For instance, the first size may be smaller than the second size or vice versa.

Moreover, the template object may be displayed by a first application, and the reference object and the target object may be displayed by a second application. In other words, the first and second applications may be independent of one another. Preferably, the first application does not have access to program instructions or memory used by the second application. Additionally, the first application may not be able to communicate with the second application.

At steps 608 and 610, the template object may be rotated and moved, respectively, so that it aligns with at least the matched part of the target object. Alternatively, the target object may be rotated or moved to achieve the same goal. Once the user is satisfied with the size and alignment of the template object, the first application may store or otherwise record the template object's size, as well as other information that may be provided. It should be noted that steps 608 and 610 may occur in any order. Thus, the template object may be rotated then moved, or moved then rotated.

Flow chart 700 is arranged according to another example embodiment. At step 702, a first virtual size of a reference object is determined. Preferably, the reference object is of a first physical size that is known, and the reference object was previously displayed on a computer screen. Thus, the first virtual size of the reference object may be expressed as a number of pixels. In this way, the magnification level of the reference object, which can be expressed as a ratio of pixels per millimeter (or any other unit of measure), can be determined.

At step 704, at least one of a template object and a target object is displayed at a second virtual size so that the template object substantially matches at least a section of the target object. The target object may have been previously displayed on the computer screen at the same magnification level as the reference object, and may be a radiographic picture depicting a bone structure. Preferably, the second virtual size is based on the determined magnification level. For example, given the ratio of pixels per millimeter, the second virtual size can be based on the number of pixels required to display the template object at the same magnification level at which the target object is displayed. If the template object is displayed at the second virtual size, then preferably the second virtual size of the template object is chosen from a discrete range of virtual sizes, where each of these virtual sizes may correspond to a particular make, model, brand, or size of implant hardware.

At step 706, at least part of the template object is overlaid on or with the target object. This overlaying may include displaying the template object or the target object in a transparent or semi-transparent fashion. Although not shown in FIG. 7, the template object may also be rotated or moved to substantially align at least part of the template object with the matched section of the target object.

At step 708, a second physical size of the template object may be determined based on the first physical size, the first virtual size and the second virtual size. Preferably, the second physical size is determined by applying the magnification level to the second virtual size in order to determine the ratio of millimeters per pixel (or any other unit of measure) for the displayed target object.

As described in the context of flow chart 600, the template object may be displayed by a first application, and the reference object and the target object may be displayed by a second application. Thus, the first and second applications may be independent of one another such that the first application does not have access to program instructions or memory used by the second application. Additionally, the first application may not be able to communicate with the second application.

V. Additional Features for Templating Applications

The templating application described by the embodiments herein has a valuable characteristic, in that physicians may spend a significant portion of their time using this software to perform their tasks. This virtual "face time" with busy physicians can be helpful for implant hardware vendors, as these vendors often find it difficult to schedule meetings with physicians. Thus, the templating application may include one or more windows, banners, or sections that are used for purposes not directly related to fitting templates to bone structures. In these windows, banners, or sections, the templating application may display information regarding just one vendor or multiple vendors.

For instance, before, during, or after a templating a procedure, the templating application may display some form of advertisement to the user. This advertisement may be contextual, and therefore display information related to the templating procedure being performed. Thus, if the user is fitting a template of hip replacement implant hardware, the advertisement might display additional types of hip replacement implant hardware, new models of implant hardware, or upcoming training courses on hip replacement procedures. Thus, the advertisement may include images, text, or both, and any included images may be static or animated. Further, the images or text may incorporate hyperlinks to additional information, such as content found on one or more web logs (blogs), message boards or other types of online forums, social networking web sites, or other content.

It should be understood that blogs may be online diaries or reporting sites, on which one or more individuals may publish commentary, news, opinions, or other items of interest. Blog entries may be published regularly or irregularly, and may include text and other types of media. There are millions of blogs on the Internet. Additionally, message boards may include online discussion forums that typically involve multiple users posting articles or messages in discussion threads. These threads may be organized logically into specific or general topics or subjects. Like blog entries, message board posts may include text as well as other types of media. Further, social networking web sites may be online communities of individuals connected by common interests, background, or activities. These individuals may be able to create, share, and collaborate on various forms of content. Popular social networking web sites include WIKIPEDIA®, YOUTUBE®, TWITTER®, FACEBOOK®, FLICKR®, and MYSPACE®.

In an illustrative example, a physician may initiate the templating application. In response, the templating application may display an advertising window containing a graphical link to an implant hardware vendor's web site. As the physician chooses a template from a given vendor, the window may display the vendor's latest hardware offerings. During the templating procedure, the window may display dates and times of the vendor's upcoming training courses. After the templating is complete, the physician may be offered the opportunity to read blogs, forums, or social networking sites that feature content related to the type of procedure for which the physician performed the templating.

Advantageously, from what is offered in the advertising window, the physician may be able to obtain information that he or she would not have otherwise known existed. Compared to traditional print advertising, which is largely unread, advertising in the templating application can be focused on the particular interests of a specific user.

VI. Conclusion

Example embodiments have been described above. Those skilled in the art will understand, however, that changes and modifications may be made to these embodiments without departing from the true scope and spirit of the invention, which is defined by the claims. Functionally equivalent methods and apparatuses within the scope of the disclosure, in addition to those enumerated herein, will be apparent to those skilled in the art from the foregoing descriptions. Such modifications and variations are intended to fall within the scope of the appended claims. It is also to be understood that the terminology used herein is for the purpose of describing particular embodiments only, and is not intended to be limiting.

For instance, the term "physician" generally refers to any medical professional who may perform any templating function discussed herein. This individual need not be a licensed doctor. Further, the term "user" applies to any person or thing that may interact with the templating applications. Also, the term "bone structure" refers to one or more bones that may be coupled to one or more joints or other parts of a skeletal system.

It should be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Despite the focus of these example embodiments, the methods and devices disclosed herein are not limited to use in joint replacement procedures or orthopedics in general. In addition to the uses described above, the present invention can be used in fields such as architecture, space planning, and civil engineering, or any other field where a template is matched to features depicted in an image. Furthermore, the methods and devices disclosed herein may operate on or make use of a wide range of physical or logical computer hardware components, and may be implemented on any type of software platform.

What is claimed is:

1. A method for a computing device to substantially match a template object to a target object in an image acquired of a subject, wherein the template object represents at least a section of the target object, and the target object is of a given scale, the method comprising:
   displaying the target object with a first processor system executable application;
   performing a screen capture of at least a portion of the target object with a second processor system executable application prior to overlaying the template object on the target object;
   based on a reference object of the given scale in the image, the computing device adjusting the target object in the second processor system executable application from a first size to a second size by measuring the reference object displayed with the first processor system executable application, such that the template object substantially matches at least the section of the target object; and
   the computing device overlaying the template object and the target object and automatically rotating and moving the template object to substantially align the template object with at least the matched part of the target object.

2. The method of claim 1, wherein adjusting at least one of the template object and the target object occurs before selecting an implant device based on the template object by overlaying the template object and the target object.

3. The method of claim 2, wherein the computing device adjusts the template object, and wherein the first size of the template object is chosen from a discrete range of sizes, wherein and the second size of the template object is based on applying the given scale to the first size.

4. The method of claim 1, wherein the target object depicts a radiographic picture of a bone, and wherein the template object represents a replacement part for the bone.

5. The method of claim 1, wherein the target object depicts a radiographic picture of a bone, and wherein the template object represents a fixation implant for the bone.

6. The method of claim 1, wherein overlaying the template object and the target object comprises displaying the template object in a semi-transparent fashion.

7. The method of claim 1, wherein overlaying the template object and the target object comprises displaying the target object in a semi-transparent fashion.

8. A computing device comprising:
   a data storage to store program instructions of a first application; and
   a processor to execute program instructions of the first application, to:
   based on measuring a reference object of a given scale, adjust a target object from a first size to a second size, wherein a template object represents at least a section of the target object, wherein the target object is of the given scale, and wherein the adjusting results in the template object substantially matching at least the section of the target object, performing a screen capture of at least a portion of the target object with the first application prior to overlaying the template object on the screen capture of the target object, and overlay the template object on the screen capture of the target object;

wherein the template object is displayed with the first application of a display device and the target object and the reference object are displayed with a second application on the display device;

wherein the first application and the second application are independent and executed by the processor.

9. The computing device of claim 8, wherein adjusting at least one of the template object and the target object occurs before overlaying the template object and the target object.

10. The computing device of claim 8, wherein the computing device adjusts the template object, and wherein the first size of the template object is chosen from a discrete range of sizes, wherein and the second size of the template object is based on applying the given scale to the first size.

11. The computing device of claim 8, further comprising: a display device;

wherein the target object depicts a radiographic picture of a bone that is transferred from a server for display on the display device, and wherein the template object represents a replacement part for the bone for display on the display device as the overlay on the screen capture of the target object.

12. The computing device of claim 8, wherein overlaying the template object and the target object comprises displaying the template object in a semi-transparent fashion.

13. The method of claim 1, wherein the user selects the template object prior to the computing device overlaying the template object and the target object and automatically rotating and moving the template object.

14. A method to substantially match a template object containing an outline in the shape of the implant to a target object containing a bone image, wherein the template object represents at least a section of the target object, the method comprising:

displaying the template object with a first processor system executable application on a display device, wherein the template object is selected to associate with a bone structure in the bone image;

displaying the target object with a second processor system executable application;

performing a screen capture of at least a portion of the target object in the bone image with the first processor system executable application prior to overlaying the template object on the screen capture of the target object;

adjusting the target object in the first processor system executable application based on a reference object of a given scale with a computing device from a first size to a second size based on measuring a size of a radiographic marker with the first processor system executable application in the target object displayed in the second processor system executable application; and overlaying the template object on the target object displayed on the display device with the first processor system executable application to allow at least one of rotating or moving the selected template object so that the template object overlays at least a section of the bone image depicted by the target object;

wherein the first processor system executable application is independent and separate from the second processor system executable application and the template object is displayed overlaid on at least one of the reference object or the target object on the display device;

wherein the first application does not have access to program instructions used by the second application and the first application does not have access to memory used by the second application.

15. The method of claim 14, further comprising:

displaying with the first processor system executable application on the display device a graphical user interface design including a heads-up display including at least one floating dialog box that appears somewhat near the template object that allows a user to specify at least one feature of the template object.

16. The method of claim 14, wherein obtaining the image of the target object includes transferring the image from a file transfer program including at least one of an email application, a web browsing application, a messaging application.

17. The method of claim 16, wherein the second processor system executable application is the email application and the template object is overlayed on the image of target object displayed by the email application.

18. A method for sizing a template object with a processor executing instructions, comprising:

operating the processor to communicate with a server to receive an image of a target object and a reference object with a first application;

viewing a display of the template object with a second application;

based on a measured size of the reference object with the second application, operating the processor to adjust at least one of the template object or the target object from a first size to a second size such that the template object substantially matches at least a first section of the target object; and after the adjustment, moving the template object that is overlayed on the target object to align the template object with at least a portion of the to allow for a selection of an implant;

wherein the adjustment is based on operating the processor to:

determine a first virtual size of a displayed reference object, wherein the reference object is of a first physical size, displaying at least one of the template object and a target object at a second virtual size so that the template object substantially matches at least a second section of the target object, and wherein determining the first virtual size is performed by a processor executing a program instruction of a second application to, based on the displayed reference object, adjust at least one of the template object or the target object;

wherein overlaying the target object with at least the part of the template object is performed by the processor executing the program instructions of the second application;

wherein the first application does not have access to memory or instructions of the second application and the second application does not have access to memory or instructions of the first application.

19. The method of claim 18, wherein based on the measured size of the reference object, operating the processor to adjust at least one of the template object or the target object from a first size to a second size includes adjusting only the template object from the first size to the second size.

20. The method of claim 19, further comprising:
determining a second physical size of the template object based on at least one of the first physical size, the first virtual size, or the second virtual size to select the implant.

21. The method of claim 20, wherein determining the first virtual size of the displayed reference object includes determining a magnification level of the reference object expressed as a ratio of pixels per unit of measure based on the first physical size that is known;
wherein determining the second physical size of the template object is based on all of the first physical size, the first virtual size, and the second virtual size and applying the magnification level including the ratio of pixels per unit of measure to the second virtual size.

22. The method of claim 21, further comprising:
automatically displaying information to a user relevant to the displayed template object including at least advertising, hardware offerings, training course schedules, content related to the type of procedure for which the template object is useful.

23. The method of claim 18, wherein adjustment is further based on operating the processor to suggest rotating and moving the template object by the second application.

24. A method of operating a computing device to substantially match a template object to a target object, wherein the template object represents at least a section of the target object, the method comprising:
operating the computing device to select the target object by communication from the computing device to an image storage system;
operating the computing device to obtain a screen capture of the target object;
viewing a display of the template object on a display device of the computing device;
adjusting at least one of the template object or the screen capture of the target object from a first size to a second size based on measuring a reference object of a given scale with the computing device; and
moving the template object overlayed on the screen capture of the target object displayed on the display device to align the template object with a selected portion of the template object;
wherein the template object is configured to allow selection of an implant based on viewing the moved template object when aligned;
wherein a first processor system executable application measures the reference object displayed by a second processor system executable application.

25. The method of claim 24, wherein the first processor system executable application is independent and separate from the second processor system executable application;
wherein the first application does not have access to program instructions used by the second application and the first application does not have access to memory used by the second application;
wherein the first processor system executable application is configured to perform the screen capture and move the template object based on input from a user;
wherein the second processor system executable application is configured to transfer the target object.

* * * * *

UNITED STATES PATENT AND TRADEMARK OFFICE
CERTIFICATE OF CORRECTION

Page 1 of 1

PATENT NO.         : 8,908,937 B2
APPLICATION NO.    : 12/832724
DATED              : December 9, 2014
INVENTOR(S)        : Paul Richard Beck It is certified that error appears in the above-identified patent and that said Letters Patent is hereby corrected as shown below:

In the Claims,

Claim 14, Column 19, Line 56, after "size" first occurrence, insert --at least by--.

Claim 18, Column 20, Line 39, after "the", insert --target object--.

Claim 24, Column 22, Line 8, after "computing device;", insert --from a first size to a second size;--.

Signed and Sealed this
Twelfth Day of May, 2015

Michelle K. Lee
*Director of the United States Patent and Trademark Office*